United States Patent
Leclaire et al.

(10) Patent No.: US 10,571,449 B2
(45) Date of Patent: Feb. 25, 2020

(54) METHOD FOR DETECTING, CAPTURING AND/OR RELEASING CHEMICAL ELEMENTS

(71) Applicants: UNIVERSITE D'AIX-MARSEILLE, Marseilles (FR); CENTRE NATIONAL DE LA RECHERCHE SCIENTIFIQUE, Paris (FR); ECOLE CENTRALE DE MARSEILLE, Marseilles (FR); UNIVERSITE CLAUDE BERNARD LYON 1 (UCBL), Villeurbanne (FR)

(72) Inventors: Julien Leclaire, Marseilles (FR); Gabriel Canard, Marseilles (FR); Frédéric Fotiadu, Marseilles (FR); Guillaume Poisson, Marseilles (FR)

(73) Assignees: UNIVERSITE D'AIX-MARSEILLE, Marseilles (FR); CENTRE NATIONAL DE LA RECHERCHE SCIENTIFIQUE, Paris (FR); ECOLE CENTRALE DE MARSEILLE, Marseilles (FR); UNIVERSITE CLAUDE BERNARD LYON 1 (UCBL), Villeurbanne (FR)

( * ) Notice: Subject to any disclaimer, the term of this patent is extended or adjusted under 35 U.S.C. 154(b) by 379 days.

(21) Appl. No.: 14/892,317

(22) PCT Filed: May 20, 2014

(86) PCT No.: PCT/FR2014/051172
§ 371 (c)(1),
(2) Date: Nov. 19, 2015

(87) PCT Pub. No.: WO2014/188115
PCT Pub. Date: Nov. 27, 2014

(65) Prior Publication Data
US 2016/0097755 A1     Apr. 7, 2016

(30) Foreign Application Priority Data
May 20, 2013  (FR) ..................................... 13 54510

(51) Int. Cl.
G01N 31/02     (2006.01)
G01N 33/20     (2019.01)

(52) U.S. Cl.
CPC ............ *G01N 33/20* (2013.01); *G01N 31/02* (2013.01)

(58) Field of Classification Search
None
See application file for complete search history.

(56) References Cited

U.S. PATENT DOCUMENTS

2004/0234958 A1*  11/2004  Smith .................. C07D 213/53
                                                       435/6.12

FOREIGN PATENT DOCUMENTS

FR          2 969 504         6/2012

OTHER PUBLICATIONS

Vitanova et al (J. Organometallic Chemistry 690:5182-97) (Year: 2005).*
Aresta et al (J. Chem Soc. Dalton Trans. pp. 3359-3363) (Year: 1995).*
Zhao et al (Inorganic Chemistry 51:5994-6 including supporting information) (Year: 2012).*
Zhao et al (Inorganic Chemistry 51:5994-6 supporting information) (Year: 2012).*
Albrecht (J. Inclusion Phenomena and Macrocyclic Chemistry 36: 127-51) (Year: 2000).*
Perkin Elmer (2400 Series II CHNS/O Elemental Analyzer Brochure) (Year: 2011).*
Calderazzo et al (Inorganic Chemistry 17:471-3) (Year: 1978).*
Dell'Amico et al (Chem. Rev. 103: 3857-97) (Year: 2003).*
Calderazzo et al II (Inorganic Chemistry 17:474-9) (Year: 1978).*
Binnemans, K., et al., "Recycling of rare earths: a critical review," *Journal of Cleaner Production*, Jan. 5, 2013, vol. 51, pp. 1-22.
Canard, G., et al., "Effective Concentration as a Tool for Quantitatively Addressing Preorganization in Multicomponent Assemblies: Application to the Selective Complexation of Lanthanide Cations," *Journal of the American Chemical Society*, Jan. 1, 2008, vol. 130, No. 3, pp. 1025-1040.
Leclaire, J., et al., "$CO_2$ Binding by Dynamic Combinatorial Chemistry: An Environmental Selection," *Journal of the American Chemical Society*, Mar. 17, 2010, vol. 132, No. 10, pp. 3582-3593.
Written Opinion in International Application No. PCT/FR2014/051172, dated Sep. 10, 2014, pp. 1-4.
Septavaux, J. et al. "Simultaneous $CO_2$ capture and metal purification from waste streams using triple level dynamic combinatorial chemistry" pp. 1-10.
Poisson, G. et al. "Straightforward and selective metal capture through $CO_2$-induced self-assembly" *Green Chem.*, 2016, pp. 6436-6444, vol. 18.

* cited by examiner

*Primary Examiner* — Christopher M Gross
(74) *Attorney, Agent, or Firm* — Saliwanchik, Lloyd & Eisenschenk (57) ABSTRACT

The invention relates to a method suitable for detecting, capturing and/or selectively releasing chemical elements selected from poor metals, alkalines, alkaline earths, actinides and rare earths. Said method involves a molecular assembly formed by at least one amine, and at least one aldehyde and/or an imine and/or $CO_2$, or an adduct formed by the contact between an amine and $CO_2$, and at least one of said chemical elements. The invention also relates to a kit for implementing said method for detection, capture and/or release.

8 Claims, 2 Drawing Sheets

METHOD FOR DETECTING, CAPTURING AND/OR RELEASING CHEMICAL ELEMENTS

CROSS-REFERENCE TO RELATED APPLICATION

This application is the U.S. national stage application of International Patent Application No. PCT/FR2014/051172, filed May 20, 2014.

The present invention relates to an appropriate process for the selective detection, capture and/or release of chemical elements chosen from p-block metals, alkali metals, alkaline earth metals, actinide metals and rare earth metals. These processes employ a molecular assembly formed of at least one amine, at least one aldehyde and/or one imine and/or $CO_2$, or an adduct formed by bringing an amine and $CO_2$ into contact with at least one of these chemical elements. The invention also relates to a kit for the implementation of the detecting, capturing and/or releasing process.

INTRODUCTION

Some chemical elements, such as actinide metals and rare earth metals, are widely used today for numerous applications, for example in batteries, magnets or low-power lamps. Even if rare earth metals are elements abundantly present in the earth's crust, the world demand for these elements for new technologies, which is ever increasing, and the Chinese monopoly on their production make them strategic elements.

Concentrates of rare earth metals as a mixture are obtained after several stages of separation of the ores extracted in order to obtain very high purity levels. Rare earth metal concentrates can also be obtained from post-consumption waste by specialist recyclers. In this context, there is an increasing preoccupation relating to the possibilities of separating these elements from one another or from other elements. To date, processes for the selective sorting of elements of this type are based mainly on countercurrentwise liquid/liquid extraction processes, after ionic chromatography and selective precipitation have been abandoned. These methods are expensive in terms of infrastructures, of time and of energy, with low capacities and performances.

A novel separation approach capable of considerably reducing operating and infrastructure costs in comparison with the liquid/liquid separation technology used in the rare earth metal industry has been developed. Its principle is based on a recently published paper which describes the self-assembling of specific molecular bricks in the presence of $CO_2$ (Leclaire et al., *J. Am. Chem. Soc.*, 2010, 132, pp. 3582-3593) and envisages the use of these molecular assemblies to separate different components of a mixture.

Unexpectedly, it has been demonstrated that systems analogous to those described in the above paper, deploying simple organic bricks, also make possible the formation of a sophisticated architecture involving chemical elements chosen from p-block metals, alkali metals, alkaline earth metals, actinide metals and rare earth metals. The formation of these assemblies results in their precipitation and thus makes it possible to envisage their use in processes for detecting, capturing and/or releasing the above-mentioned chemical elements which are inexpensive and simple to carry out and which can use a waste product harmful to the environment ($CO_2$).

SUMMARY OF THE INVENTION

A first subject matter of the invention is a process for detecting and/or capturing at least one chemical element chosen from p-block metals, alkali metals, alkaline earth metals, actinide metals and rare earth metals in a sample which comprises bringing:

at least one amine and at least one aldehyde and/or one imine (formed by bringing an aldehyde and an amine into contact) and/or $CO_2$, or an adduct formed by bringing an amine and $CO_2$ into contact, into contact with at least one sample capable of comprising at least one of said chemical elements. The operation of bringing these components into contact results in the formation of a molecular assembly, making it possible to detect and/or capture the desired chemical element or elements when they are present.

A second subject matter of the invention is a process for releasing at least one chemical element chosen from p-block metals, alkali metals, alkaline earth metals, actinide metals and rare earth metals which comprises the separation, at least partial, preferably total, of the components of an assembly formed by bringing:

at least one amine and at least one aldehyde and/or one imine and/or $CO_2$, or an adduct formed by bringing an amine and $CO_2$ into contact, into contact with a sample comprising said chemical element or elements.

A third subject matter of the invention is a process for the formation of a molecular assembly which comprises bringing:

at least one amine and at least one aldehyde and/or one imine (formed by bringing an aldehyde and an amine into contact) and/or $CO_2$, or an adduct formed by bringing an amine and $CO_2$ into contact, into contact with at least one sample comprising at least one chemical element chosen from p-block metals, alkali metals, alkaline earth metals, actinide metals and rare earth metals.

A final subject matter of the invention is a kit for detecting, capturing and/or releasing at least one chemical element chosen from p-block metals, alkali metals, alkaline earth metals, actinide metals and rare earth metals which comprises at least one amine and at least one aldehyde or one imine and/or $CO_2$, or an adduct formed by bringing an amine and $CO_2$ into contact.

DETAILED DESCRIPTION OF THE INVENTION

The processes for detecting, capturing and/or releasing chemical elements according to the invention are based on the formation of molecular assemblies when the chemical elements are brought into contact with at least one amine and at least one aldehyde and/or one imine and/or $CO_2$ or with an adduct formed by bringing an amine and $CO_2$ into contact. The formation of such an assembly is detected by the formation of a precipitate within the medium comprising the various components.

In one embodiment, the invention relates to a process for detecting and/or capturing at least one chemical element chosen from alkali metals, alkaline earth metals, actinide metals and rare earth metals in a sample which comprises bringing at least one amine, at least one aldehyde and/or one imine, optionally $CO_2$, and optionally an adduct formed by bringing an amine and $CO_2$ into contact, and at least one of said chemical elements into contact.

Description of the different components of the assemblies according to the invention

—Aldehyde

An aldehyde according to the invention is a compound comprising at least one aldehyde CHO functional group. Thus, the aldehyde can be of the general formula:

in which R1 is chosen from alkyl, alkenyl, alkynyl, cycloalkyl, cycloalkenyl and cycloalkynyl groups and aromatic groups, the hydrocarbon chain of which is optionally interrupted by at least one heteroatom chosen from N, O and S, and which are optionally substituted by at least one substituent. Preferably, the substituents do not independently comprise amine (—NHR or —$NH_2$), hydrazine (—NH—$NH_2$), hydrazide (C(O)—NH—$NH_2$), or hydroxylamine (—O—$NH_2$). Preferably, the substituents are as defined below.

Preferably, the aldehyde is of the general formula:

(II)

in which A represents a hydrocarbon ring chosen from cycloalkyls, cycloalkenes, cycloalkynes and aromatic groups comprising n ring members, n being between 5 and 7; preferably, n has the value 5 or 6. In particular, the hydrocarbon ring is a phenyl. The hydrocarbon ring can optionally be interrupted by at least one heteroatom chosen from N, O and S. Each $R_n$ substituent is chosen from a hydrogen atom, an aldehyde CHO, a hydroxyl —OH group, a thiol —SH, a halogen atom, an alkoxyl group and a $C_1$-$C_{20}$, preferably $C_1$-$C_3$, alkyl. In a preferred embodiment, each alkyl group does not independently comprise any amine (—NHR or —$NH_2$), hydrazine (—NH—$NH_2$), hydrazide (C(O)—NH—$NH_2$), or hydroxylamine (—O—$NH_2$) substituent. At least one $R_n$ comprises, and preferably is, an aldehyde CHO.

In the present invention, an alkyl group denotes a linear or branched $C_1$-$C_{20}$, preferably $C_1$-$C_6$, in particular $C_1$-$C_3$, hydrocarbon group. Preferably the alkyl group is chosen from methyl, ethyl, n-propyl, isopropyl, n-butyl, sec-butyl, tert-butyl, n-pentyl and n-hexyl groups. The alkyl group can optionally be interrupted by at least one heteroatom chosen from N, O and S. The alkyl group can optionally be substituted, in particular by at least one group chosen from hydroxyls (—OH), alkoxyls (—OR), thiols (—SH), thioethers (—SR), carbonyls (—CHO or —C(O)R), carboxyls (—COOH or —COOR), amines (—$NH_2$), hydrazines (—NH—$NH_2$), hydrazides (C(O)—NH—$NH_2$), hydroxylamines (—O—$NH_2$), halogens, imines (—CH=NR), oximes (—CH=NOR or —CH=NOH), hydrazones (—CH=N—NHR), acylhydrazones (—CH=N—NH—C(O)—R), aminals (—CH(NHR)—NHR'), oxazolidines (—CH(OR)—NHR') and thiazolidines (—CH(SR)—NHR'), where R and R' are preferably independently unsubstituted hydrocarbon alkyl groups and comprise solely simple bonds.

An alkenyl group denotes an alkyl group as defined above additionally comprising at least one C=C double bond.

An alkynyl group denotes an alkyl group as defined above additionally comprising at least one C≡C triple bond.

The cycloalkyl, cycloalkenyl and cycloalkynyl groups respectively represent cyclic alkyl, alkenyl and alkynyl groups.

An aromatic group is a group comprising at least one flat ring comprising a conjugated π system formed of double bonds and/or of lone pairs, in which each atom of the ring comprises a p orbital, the p orbitals overlap and the delocalization of the π electrons results in a decrease in the energy of the molecule. Preferably, an aromatic group is chosen from phenyl, pyridinyl, pyrimidinyl, pyrazinyl, triazinyl, furanyl, thiophenyl, pyrrolyl, imidazolyl, thiazolyl, oxazolyl and naphthyl groups. Highly preferably, the aromatic group is a phenyl.

An alkoxyl (—O-alkyl) group denotes an alkyl group as defined above, said alkyl group being connected to the remainder of the molecule via an oxygen atom.

A halogen denotes an atom chosen from fluorine, bromine, chlorine and iodine, preferably chlorine or bromine.

Preferably, the aldehyde is of formula (III)

in which at least one from $R_1$ to $R_6$ is an aldehyde group and the others are chosen from hydrogen atoms, $C_1$-$C_{20}$ alkyl groups, hydroxyl groups, thiol groups, halogen atoms and $C_1$-$C_{20}$ alkoxyl groups.

In a preferred embodiment, the aldehyde is chosen from the following compounds:

A

B

Highly preferably, the aldehyde is chosen from compounds B and C; in particular, the aldehyde is compound C.

The aldehydes according to the invention can be obtained by any appropriate synthesis route known in the art. Thus, for example, some aldehydes of the invention can be obtained by the Duff reaction with hexamethylenetetramine.

—Amine

An amine according to the invention is a compound comprising at least one, preferably one or two, primary amine —$NH_2$ or secondary amine —NHR functional groups, where R is as described above, and optionally at least one tertiary amine functional group. The amine according to the invention can be of general formula (IV) R2-NH—R3, in which R2 is chosen from alkyl, alkenyl, alkynyl, cycloalkyl, cycloalkenyl and cycloalkynyl groups and aromatic groups, the hydrocarbon chain of which is optionally interrupted by at least one heteroatom chosen from N, O and S and which are optionally substituted by at least one substituent as defined above, which substituent preferably does not comprise an aldehyde CHO; R3 is chosen from a hydrogen atom, alkyl, alkenyl, alkynyl, cycloalkyl, cycloalkenyl and cycloalkynyl groups and aromatic groups, the hydrocarbon chain of which is optionally interrupted by at least one heteroatom chosen from N, O and S and which are optionally substituted by at least one substituent as defined above. Preferably, the substituents do not independently comprise an aldehyde CHO.

In one embodiment, the amine comprises just one amine functional group.

In a second embodiment, the amine comprises at least 2 amine functional groups, preferably at least 3, at least 4 or at least 5 amine functional groups. In particular, the amine is such that R3 is a hydrogen atom and R2 is an alkyl group, the hydrocarbon chain of which is interrupted by at least one nitrogen atom.

In a specific embodiment, the process according to the invention comprises, in particular, bringing an amine comprising at least 2 amine functional groups into contact with an imine formed by reaction of an aldehyde with an amine comprising just one amine functional group.

In another specific embodiment, the process according to the invention comprises, in particular, bringing an amine comprising at least 2 amine functional groups into contact with an adduct formed by reaction of an amine comprising just one amine functional group with $CO_2$.

Preferably, an amine according to the invention is chosen from the following compounds:

ethylenediamine tris(2-aminoethyl)amine a polyethylenimine, in particular a linear or branched polyethylenimine, in particular diethylenetriamine or triethylenetetramine piperazine cis-1,4-cyclohexanediamine trans-1,4-cyclohexanediamine and phenylenediamine In a preferred embodiment, the amine is chosen from ethylenediamine, diethylenetriamine 2, triethylenetetramine 6 and tris(2-aminoethyl)amine.

Highly preferably, the amine is compound 2.

The aldehydes and amines of the invention are chosen by a person skilled in the art as a function of their structural characteristics, for example, the number of reactive (aldehyde and/or amine) functional groups and/or their molar mass. The formation of the assemblies involves the formation of imine bonds by reaction of the amine groups of the amines with the aldehyde groups of the aldehydes. Bonds of hydrazone, oxime, aminal, oxazolidine, thiazolidine and/or carbamate types can also be deployed.

—Imine

An imine according to the invention is obtained by bringing an aldehyde according to the invention into contact with an amine of formula (IV) as defined above. Preferably, the amine comprises just one amine functional group. Preferably, R2 is an unsubstituted hydrocarbon alkyl group comprising solely single bonds and R3 is a hydrogen atom; in particular, the amine is n-butylamine. According to an embodiment of the invention, all the CHO groups of the aldehyde according to the invention react with the amine. According to another embodiment of the invention, only some CHO groups of the aldehyde react with the amine. Thus, an imine according to the invention can comprise both CHO groups and imine groups.

Preferably, an imine according to the invention is chosen from the following compounds:

Highly preferably, the imine is chosen from compounds AI₃ and BI₃; in particular, the polyimine is compound BI₃.

—Adduct Formed by Bringing an Amine and CO₂ into Contact

An adduct according to the invention is capable of being obtained, and preferably is obtained, by bringing an amine according to the invention into contact with carbon dioxide. The adduct can be a carbamate. Depending on the amine used, the adduct can also be an aminal (if the amine is an ethanediamine or a propanediamine), an oxazolidine (if the amine is an aminoethanol or an aminopropanol) or a thiazolidine (if the amine is an aminoethanethiol or an aminopropanethiol).

—Carbon Dioxide

An assembly formed according to the process of the invention can optionally comprise carbon dioxide. The carbon dioxide used can result from a human activity, of which it represents a waste product; for example, it can originate from combustion flue gases, refinery gas, cement works gas or blast furnace gas.

—Chemical Element

The assembly formed according to the process of the invention comprises at least one chemical element chosen from p-block metals, alkali metals, alkaline earth metals, actinide metals and rare earth metals.

In the context of the present invention, p-block metals denote metal elements from the p group of the Periodic Table. The group of p-block metals comprises aluminum $^{13}$Al, gallium $^{31}$Ga, indium $^{49}$In, tin $^{50}$Sn, thallium $^{81}$Tl, lead $^{82}$Pb, bismuth $^{83}$Bi, polonium $^{84}$Po and flerovium $^{114}$Fl. Preferably, the p-block metal is indium.

In the context of the present invention, alkali metals denote the elements of the first column of the Periodic Table, with the exception of hydrogen. The group of alkali metals comprises lithium $^{3}$Li, sodium $^{11}$Na, potassium $^{19}$K, rubidium $^{37}$Rb, cesium $^{55}$Cs and francium $^{87}$Fr. Preferably, the alkali metal is cesium.

In the context of the present invention, alkaline earth metals denote the elements of the second column of the Periodic Table. The group of alkaline earth metals comprises beryllium $^{4}$Be, magnesium $^{12}$Mg, calcium $^{20}$Ca, strontium $^{38}$Sr, barium $^{56}$Ba and radium $^{88}$Ra.

In the context of the present invention, actinide metals denote actinium $^{89}$Ac, thorium $^{90}$Th, protactinium $^{91}$Pa, uranium $^{92}$U, neptunium $^{93}$Np, plutonium $^{94}$Pu, americium $^{95}$Am, curium $^{96}$Cm, berkelium $^{97}$Bk, californium $^{98}$Cf, einsteinium $^{99}$Es, fermium $^{100}$Fm, mendelevium $^{101}$Md, nobelium $^{102}$No and lawrencium $^{103}$Lr. Preferably, the actinide metals are chosen from thorium and uranium.

In the context of the present invention, rare earth metals denote scandium $^{21}$Sc, yttrium $^{39}$Y and the fifteen lanthanide metals. Lanthanide metals denote lanthanum $^{57}$La, cerium $^{58}$Ce, praseodymium $^{59}$Pr, neodymium $^{60}$Nd, promethium $^{61}$Pm, samarium $^{62}$Sm, europium $^{63}$Eu, gadolinium $^{64}$Gd, terbium $^{65}$Tb, dysprosium $^{66}$Dy, holmium $^{67}$Ho, erbium $^{68}$Er, thulium $^{69}$Tm, ytterbium $^{70}$Yb and lutetium $^{71}$Lu. Preferably, the rare earth metals comprise lanthanum and/or lutetium.

According to a specific embodiment, at least one of the chemical elements is (a) rare earth metal(s), in particular La and/or Lu.

The chemical element can be brought into contact with the other components in the element form without bonding to another atom or in the form of a derivative, such as a salt or a complex. For example, the element can be brought into contact with the other components in the form of a nitrate, of a trifluoroacetate or of an acetate.

The sample on which the detecting and/or capturing process according to the invention is carried out can be any type of sample capable of comprising one or more chemical elements as defined above. It can be a sample of any origin.

The amounts (absolute or relative) of the various components of the assembly formed according to the process of the invention can be adjusted by a person skilled in the art so as to optimize the formation of the assembly. In particular, a person skilled in the art is in a position to adjust the relative proportions of aldehyde and of amine, in the case where both these types of components form part of the assembly desired, so that the ratio of the number of aldehyde functional groups to the number of amine functional groups brought together is between approximately 0.1 and approximately 10, preferably between approximately 0.8 and approximately 1.2, in particular approximately equal to 1.

In a specific embodiment, the ratio of the number of moles of amine to the number of moles of the element which it is desired to detect and/or capture is greater than or equal to 6, preferably greater than or equal to 12. Without wishing to be committed to any one theory, it appears that such a ratio makes it possible to confer properties of thermal reversibility on the precipitate which is formed in the presence of the chemical element.

Thus, it is possible, in this case, to release the chemical element according to the release process described later by simple heating, preferably to a temperature of less than or equal to 100° C.

The values of ratio of the number of moles of amine to the number of moles of the element which it is desired to detect and/or capture which make it possible to obtain such a thermal reversibility can possibly vary as a function of the counterion of the chemical element which it is desired to detect and/or capture, such as nitrate, acetate or trifluoroacetate.

In the present invention, the term "approximately" relating to a numerical value denotes an interval between plus and minus 10% of said numerical value.

Process for Detecting and/or Capturing Chemical Elements

The process for detecting and/or capturing chemical elements according to the invention comprises bringing:
- at least one amine and at least one aldehyde and/or one imine (formed by bringing an aldehyde and an amine into contact) and/or $CO_2$, or
- an adduct formed by bringing an amine and $CO_2$ into contact, into contact with at least one sample capable of comprising at least one chemical element chosen from p-block metals, alkali metals, alkaline earth metals, actinide metals and rare earth metals.

Preferably, the process comprises bringing at least one amine and $CO_2$, or an adduct formed by bringing an amine and $CO_2$ into contact, into contact with said sample.

The contacting operation can be carried out by any appropriate technique known in the art. Preferably, the contacting operation is carried out at ambient temperature, that is to say between approximately 15 and approximately 25° C.

The process can optionally in addition comprise a stage of heating the mixture obtained to a temperature higher than that of the contacting operation, preferably to a temperature between 26 and 100° C., in particular to a temperature in the vicinity of 90° C. In this case, the process also subsequently comprises a stage of controlled cooling of the mixture down to ambient temperature, as defined above.

In this case, a precipitate may be obtained during the contacting operation at ambient temperature and/or during the cooling at the end of the process.

A person skilled in the art is in a position to choose the appropriate temperature and the appropriate rate of cooling for carrying out the process as a function in particular of the chemical nature of the components of the assembly and of the thermodynamic and/or kinetic stability criteria of the latter. Thus, in order to obtain precipitation under thermodynamic and not kinetic conditions, it may be advantageous to heat the medium and then to slowly cool it. Without wishing to be committed to any one theory, it appears that a better selectivity and a better reversibility can generally be obtained with the precipitates obtained under thermodynamic conditions. At high temperature, exchanges are favored and the assembly can self-organize according to the stablest arrangement if the descent in temperature is slow, which should also make it possible to capture larger amounts of chemical elements.

A contacting operation can be carried out with or without mechanical or magnetic stirring and preferably under a controlled atmosphere, for example under an inert argon atmosphere. In the embodiments of the invention according to which the assembly is formed in the presence of $CO_2$, the controlled atmosphere preferably comprises $CO_2$; in particular, it is a $CO_2$ atmosphere. $CO_2$ can also be supplied by bubbling $CO_2$ into the liquid medium comprising the other components and the sample capable of comprising a chemical element as defined above, by addition of a carbonate and/or hydrogen carbonate salt and/or by addition of dry ice to said liquid medium.

The medium comprising the different components and the sample capable of comprising a chemical element as defined above is preferably a liquid medium.

The different components can be brought into contact either sequentially or simultaneously. Preferably, the amine, the aldehyde and/or the imine and/or the $CO_2$, or the adduct formed by bringing an amine and $CO_2$ into contact, are brought into contact simultaneously with the sample capable of comprising the chemical element. The term "simultaneously" means that the different components are brought into contact in a short period of time, for example between 0 and 30 minutes. In particular, it is on the order of less than 15 minutes, less than 10 minutes, less than 5 minutes, less than 2 minutes or less than one minute. In a preferred embodiment, the addition of the sample capable of comprising the chemical element is carried out less than 2 minutes after the mixing of the other components.

The components can be added in any order and a person skilled in the art is in a position to determine the most appropriate order of the function of the nature of each of the components. In a preferred embodiment, the sample capable of comprising the chemical element is added after the other components of the assembly.

The different components can optionally be brought into contact in the presence of other compounds, for example in the presence of at least one solvent. The solvent can be chosen from any organic or aqueous solvent appropriate for the components brought into contact, for example in order to promote their dissolution. In one embodiment, the solvent is chosen from alcohol, for example, ethanol or methanol. The solvent can be used in an anhydrous form or at different degrees of hydration. Mention may also be made, among the other compounds capable of being used, of the amines as defined above.

The formation of the assembly according to the invention is displayed by the appearance of a precipitate, which can be easily separated from the reaction medium, for example, by simple filtration and/or centrifuging.

The stage of detecting and/or capturing the chemical elements of the process according to the invention is thus carried out by observation of this precipitate after the different components have been brought into contact.

Advantageously, the detecting stage additionally comprises the comparison of the sample obtained with a similar sample which does not comprise the chemical element and which can be denoted reference sample.

Likewise, the detecting stage can additionally comprise the comparison of the sample obtained with a similar sample which comprises the chemical element.

This is because the detection of the presence (or the absence) of the element to be detected and/or captured is validated by the appearance of a precipitate in the case where the element is present and the absence of precipitate under the same conditions in the case where the element is absent.

The detecting and/or capturing process according to the invention can be used to determine the absence, the presence and/or the amount (absolute or relative) of at least one chemical element in a sample.

The detecting and/or capturing process according to the invention optionally comprises a stage of separation of the molecular assembly formed which precipitates.

The separating stage can be carried out by any appropriate technique known to a person skilled in the art. For example, the separation can be carried out by separation by settling, filtration, sieving, centrifuging, evaporation and/or distillation. Advantageously, the separating stage is carried out by a simple filtration and/or centrifuging. A person skilled in the art is in a position to adjust the parameters of the chosen technique in order to obtain an optimum separation. For example, said skilled person is in a position to adjust the parameters of the filtration, such as the nature of the filter and/or the size of the pores, and/or the parameters of centrifuging, such as the centrifuging speed, to the assembly concerned and to the sample concerned, in order to obtain optimum separation.

The sample on which the detecting and/or capturing process according to the invention is carried out can be any type of sample capable of comprising one or more chemical elements as defined above. The sample can be provided in gas, liquid or solid form; preferably, it is provided in liquid or solid form. In the case where the sample capable of comprising one or more of the targeted chemical elements does not actually comprise any of these elements, or in any case none of the elements make it possible for formation of a molecular assembly with the components specifically used, the detecting and/or capturing process according to the invention does not result in the formation of an assembly or in the observation of a precipitate. In such an embodiment, the process according to the invention is a process for detecting the absence in the sample of at least one of the chemical elements targeted. This sample can be denoted reference sample.

Preferably, the detecting and/or capturing process according to the invention is carried out within a dynamic combinatorial library comprising at least one amine and at least one aldehyde and/or imine and/or $CO_2$ or an adduct formed by bringing an amine and $CO_2$ into contact according to the invention.

The detecting and/or capturing process according to the invention exhibits undeniable advantages with respect to the current detecting and/or capturing techniques.

Thus, the capturing process according to the invention does not necessarily involve high temperatures and the process can advantageously be carried out at ambient temperature. In comparison, metallurgical processes are generally carried out at temperatures of several hundred degrees.

Next, the "molecular bricks" which form the assemblies, that is to say the aldehydes, imines and/or amines, are simple and sometimes commercially available compounds which do not require custom synthesis.

Next, the separating process involves, as sole separating stage, a simple phase separation, for example by filtration or centrifuging, which is much simpler and much more economical to carry out than other separating techniques conventionally used in this field, such as extractions or chromatographic separations, which in addition consume large amounts of solvent.

Next, the process according to the invention can make possible, in particular after release, the recycling and/or the reuse of at least some of the "molecular bricks" which form the assemblies. This possibility of reuse of the components makes it possible to limit, indeed even to suppress, the effluents at the outlet of the process.

Finally, the assemblies according to the invention can use, as capturing agent, carbon dioxide, which is a waste product.

Consequently, in comparison with the separating processes conventionally used for the chemical elements envisaged in the present invention, the process according to the present invention is clearly economical and does not consume much energy, which represents major industrial advantages.

In addition, it has been demonstrated that, under certain conditions where several chemical elements, preferably several rare earth metals, are present, an assembly according to the invention can be formed selectively with just one type of chemical element. For example, separation factors which can go up to 20 could be obtained for the separation of two rare earth metals, such as La and Lu, in the same sample by carrying out a process according to the invention.

In one embodiment of the invention, the detecting and/or capturing of at least one chemical element according to the process of the invention is selective of a chemical element.

Another subject matter of the invention is a process for releasing the element captured (or the elements captured) in the assembly, by separation or dissociation, at least partial, preferably total, of the components of the assembly. This separation can be carried out, for example, by heating, preferably at a temperature of less than or equal to 100° C., or by hydrolysis, in particular by acid or basic hydrolysis or by hydrolysis in a neutral buffered medium, at least partial, of the assembly. Preferably, the separation of the components of the assembly makes it possible to liberate and/or reform at least some of the components, preferably all the components, of the assembly. Thus, in one embodiment, the separation makes it possible to liberate and/or reform at least one component, preferably all the components, from the aldehydes, imines, amines and/or $CO_2$ forming the assembly, or one of their derivatives. The expression "one of their derivatives" denotes a chemical derivative of the aldehyde or of the amine from which a person skilled in the art knows how to reform the aldehyde or the amine. For example, the releasing process can make it possible to liberate an aldehyde in the case where an imine had been used to form the assembly. Such a separation makes it possible to reuse the components recovered, for example in a new process according to the invention, accordingly reducing the costs of carrying out the process. In the case where the dissociation of the assembly is carried out by hydrolysis, the releasing process can additionally comprise, after the hydrolysis, a stage of removal of the aqueous solution obtained, in order to make possible the reuse of the components.

In the releasing process according to the invention, the chemical element or elements chosen from p-block metals, alkali metals, alkaline earth metals, actinide metals and rare earth metals are liberated either in the chemical element form or in the form of a derivative comprising the chemical element, for example in the form of a complex or of a salt.

Another subject matter of the invention is a process for the formation of a molecular assembly which comprises bringing:

at least one amine and at least one aldehyde and/or one imine (formed by bringing an aldehyde and an amine into contact) and/or $CO_2$, or an adduct formed by bringing an amine and $CO_2$ into contact, into contact with at least one sample comprising at least one chemical element chosen from p-block metals, alkali metals, alkaline earth metals, actinide metals and rare earth metals.

The molecular assembly formed by this process is also a subject matter of the invention.

Another subject matter of the invention is a kit comprising at least one amine and at least one aldehyde and/or an imine and/or $CO_2$, or an adduct formed by bringing an amine and $CO_2$ into contact, these components being as defined above.

This kit is appropriate in particular for detecting, capturing and/or releasing at least one chemical element according to the invention. The kit can comprise at least two aldehydes and/or imines and/or at least two amines. The kit can in particular be provided in the form of a support appropriate for use in dynamic combinatorial chemistry, said support comprising several wells, in which each well comprises at least one amine and optionally at least one aldehyde and/or imine. The support can, for example, be a plate comprising wells.

Unless otherwise specified, the term "yield" denotes, in the present invention, a molar yield.

The advantages of the invention will emerge more clearly from the examples below, which are provided solely by way of illustration and without limitation of the invention.

EXAMPLES

Example 1: Preparation of the Components of the Assembly

1.1 Preparation of the Aldehydes

Aldehydes B and C were synthesized by triformylation of phenols employing a Duff reaction according to the following conditions:

compound B R = H 55%
compound C R = OH 11%

Aldehyde D was synthesized according to the following reaction:

or according to the following reaction:

Aldehyde E was synthesized according to the following reaction:

Aldehyde F was synthesized according to the following reaction:

1.2 Preparation of the Imines

Imines $A1_3$ and $B1_3$ were formed by reaction of aldehydes B and C with n-butylamine, according to the following reaction:

1.3 Preparation of the Lanthanide Salts

The lanthanum, gadolinium and lutetium salts were prepared from the oxides heated at reflux for 12 h in a mixture of trifluoroacetic acid and water.

$La(CF_3COO)_3$:

2.99 g of $La_2O_3$ are suspended in 32 ml of distilled water and 40 ml of trifluoroacetic acid are subsequently added dropwise. The mixture is stirred at 110° C. overnight. The solution is filtered through a sintered glass funnel and the filtrate is evaporated on a rotary evaporator. The solid obtained is taken up three times in ethanol. The salt (7 g) is obtained, after drying under vacuum, in the form of a white powder with a yield of 90%.

$Lu(CF_3COO)_3$:

0.5 g of $Lu_2O_3$ are suspended in 8 ml of distilled water and 10 ml of trifluoroacetic acid are subsequently added dropwise. The mixture is stirred at 110° C. overnight. The solution is filtered through a sintered glass funnel and the filtrate is evaporated on a rotary evaporator. The solid obtained is taken up three times in ethanol. The salt (1 g) is obtained, after drying under vacuum, in the form of a white powder with a yield of 90%.

$Gd(CF_3COO)_3$:

5 g of $Gd_2O_3$ are suspended in 80 ml of distilled water and 100 ml of trifluoroacetic acid are subsequently added dropwise. The mixture is stirred at 110° C. overnight. The solution is filtered through a sintered glass funnel and the filtrate is evaporated on a rotary evaporator. The solid obtained is taken up three times in ethanol. The salt (11 g) is obtained, after drying under vacuum, in the form of a white powder with a yield of 90%.

1.4 Preparation of Indium, Neodymium, Praseodymium and Lutetium Nitrates

Indium nitrate $In(NO_3)_3$, neodymium nitrate $Nd(NO_3)_3$, praseodymium nitrate $Pr(NO_3)_3$ and lutetium nitrate $Lu(NO_3)_3$ were respectively obtained by attack on indium oxide, neodymium oxide, praseodymium oxide and lutetium oxide with nitric acid. 1 g of corresponding oxide is dispersed in 20 ml of distilled water and 10 ml of 68% nitric acid are added. The mixture is heated at reflux until complete dissolution of the oxide and, after returning to ambient temperature, the solution is filtered. The nitrate salt is obtained after complete evaporation of the solvent and drying using a vane pump.

1.5 Preparation of Indium Acetate, Neodymium Acetate, Praseodymium Acetate and Lutetium Acetate Indium acetate $In(CH_3CO_2)_3$, neodymium acetate $Nd(CH_3CO_2)_3$, praseodymium acetate $Pr(CH_3CO_2)_3$ and lutetium acetate $Lu(CH_3CO_2)_3$ were respectively obtained by attack on indium oxide, neodymium oxide, praseodymium oxide and lutetium oxide with acetic acid. 1 g of corresponding oxide is dispersed in 20 ml of distilled water and 20 ml of 68% nitric acid are added. The mixture is heated at reflux until complete dissolution of the oxide and, after returning to ambient temperature, the solution is filtered. The acetate salt is obtained after complete evaporation of the solvent and drying on a vane pump.

Example 2: Demonstration of the Formation of the Assemblies by Dynamic Combinatorial Chemistry The different libraries were prepared by mixing one equivalent of aldehyde (or imine), one equivalent of metal salt and two equivalents of amine. The final concentration in the libraries is 20 mM of aldehyde or imine, 20 mM of metal salt and 40 mM of amine.

The entities used for the libraries have been abbreviated according to the numbers of compounds provided in the description. In the case of libraries prepared from aldehydes, one equivalent of n-butylamine per aldehyde functional group was introduced in order to obtain initially soluble mixtures.

The libraries were placed under a $CO_2$ or argon atmosphere. The libraries were duplicated three times.

Figure 1:
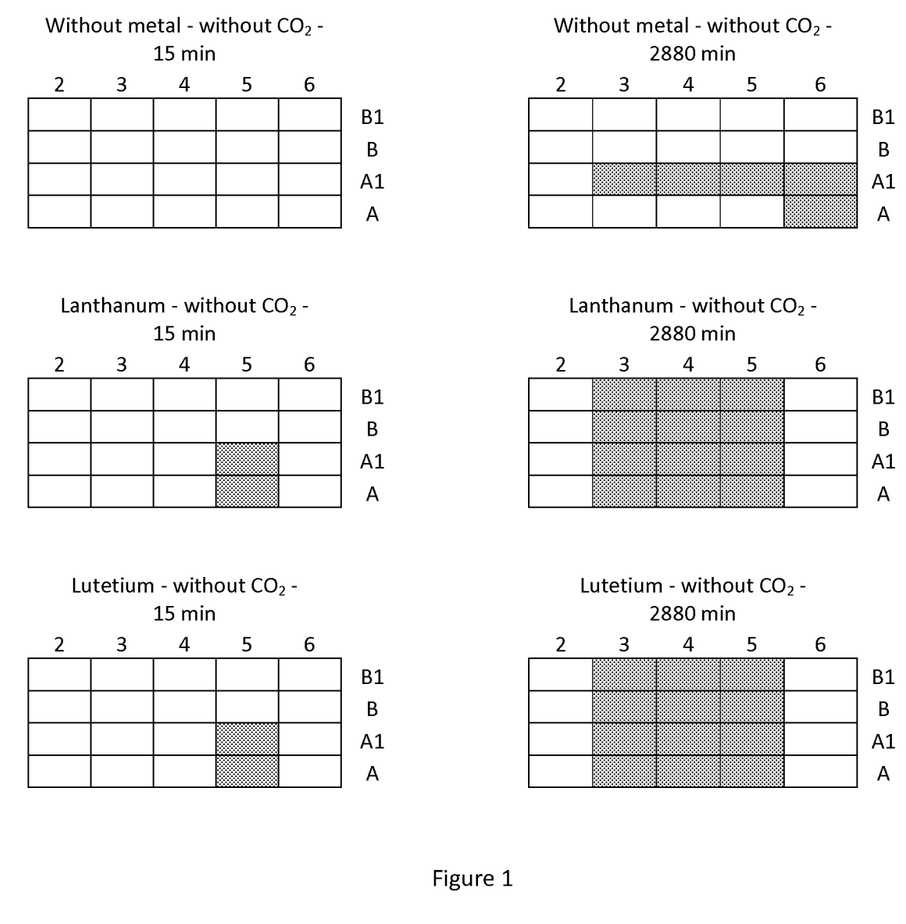
FIG. 1: Analysis of the libraries produced without addition of $CO_2$, after 15 minutes and 2880 minutes. Each compartment corresponds to the combination of an amine on the abscissa and of an aldehyde or an imine on the ordinate. A shaded compartment corresponds to the observation of a precipitate proving the formation of an assembly.
Figure 2:
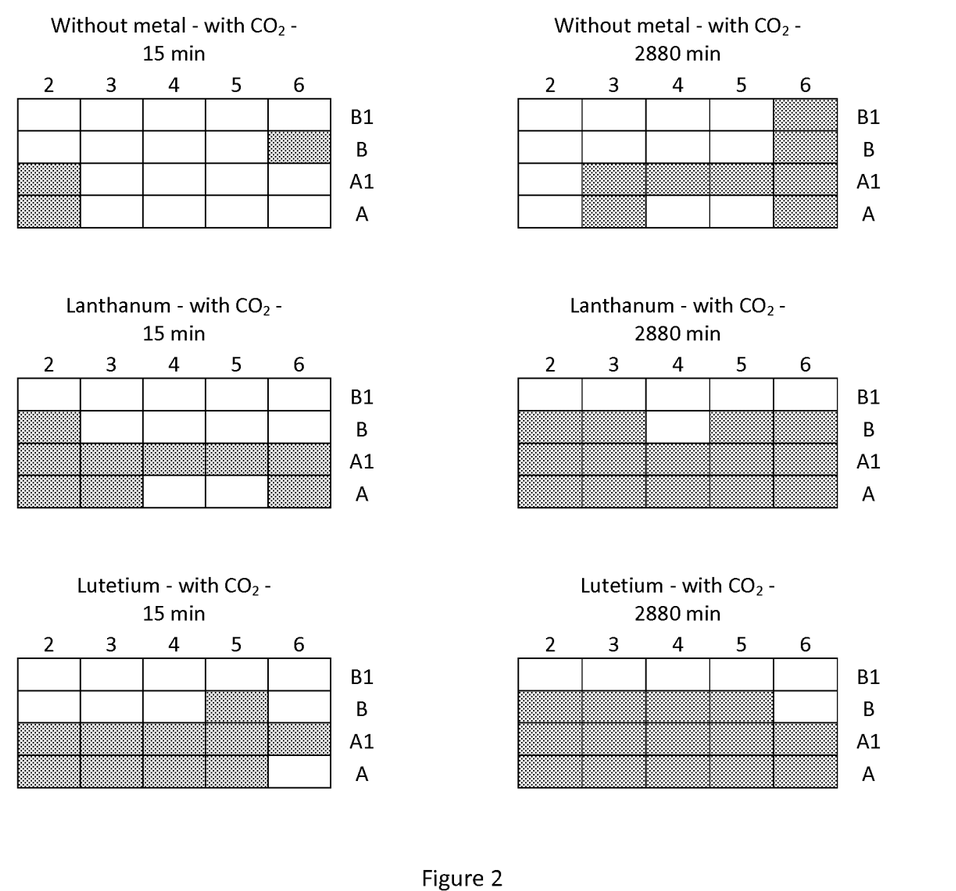
FIG. 2: Analysis of the libraries produced in the presence of $CO_2$, after 15 minutes and 2880 minutes. Each compartment corresponds to the combination of an amine on the abscissa and of an aldehyde or an imine on the ordinate. A shaded compartment corresponds to the observation of a precipitate proving the formation of an assembly.

As examples of the results obtained, FIGS. 1 and 2 combine the analysis of the libraries for each of the conditions tested; for the two experiments the times are 15 minutes and 2880 minutes. The shaded compartments in the tables correspond to the experiments for which a precipitate (characteristic of the formation of an assembly according to the invention) could be observed.

It is clear that bringing, according to the invention, an aldehyde or an imine, an amine, optionally carbon dioxide and a chemical element chosen from lanthanum and lutetium into contact has made possible the formation of an assembly according to the invention under a large number of conditions.

Experiments were also carried out while deleting from the reaction media either the aldehyde (or the imine) or the amine or the chemical element chosen from lanthanum and lutetium and, in each case, the formation of a precipitate characteristic of the formation of an assembly according to the invention could not be observed. In some cases, no precipitation took place, and in other cases, only a thin and not very copious precipitate which cannot be isolated was formed.

Example 3: Selectivity Tests

The libraries were prepared by mixing one equivalent of aldehyde (or imine), one equivalent of lanthanum salt, one equivalent of lutetium salt and two equivalents of amine. The final concentration in the libraries is 20 mM of aldehyde (or imine), 20 mM of lanthanum, 20 mM of lutetium and 40 mM of amine. The final volume of the library is 6 ml. The precipitates were separated from the observation of the presence of a precipitate onwards. The results of the elemental analysis of the precipitates obtained are combined in Table 1 below.

TABLE 1

Elemental analysis of the precipitates obtained

|  | Precipitate | C | H | La | Lu | N | La/Lu ratio |
|---|---|---|---|---|---|---|---|
| Ar | A:3:La/Lu | 28.19 | 3.45 | 12.25 | 17.41 | 6.79 | 0.70 |
|  | A:4:La/Lu | 29.78 | 3.83 | 12.01 | 16.32 | 6.32 | 0.74 |
|  | Al$_3$:3:La/Lu | 29.39 | 3.60 | 11.16 | 15.97 | 6.94 | 0.70 |
|  | C:3:La/Lu | 31.30 | 3.87 | 10.16 | 15.09 | 6.87 | 0.67 |
|  | C:4:La/Lu | 28.20 | 3.43 | 10.96 | 15.09 | 5.04 | 0.66 |
|  | C:5:La/Lu | 28.85 | 3.41 | 10.38 | 19.09 | 4.26 | 0.54 |
|  | B1$_3$:3:La/Lu | 31.07 | 3.91 | 10.73 | 14.34 | 6.99 | 0.75 |
| CO$_2$ | A:4:La/Lu | 32.51 | 4.14 | 10.91 | 12.61 | 8.37 | 0.87 |
|  | A:5:La/Lu | 29.79 | 3.82 | 12.75 | 14.87 | 6.75 | 0.86 |
|  | A:6:La/Lu | 28.62 | 3.61 | 12.27 | 13.61 | 8.95 | 0.90 |
|  | C:2:La/Lu | 37.60 | 3.94 | 2.98 | 20.22 | 4.94 | 0.15 |
|  | C:5:La/Lu | 35.40 | 3.94 | 7.00 | 18.62 | 5.02 | 0.38 |

The elemental analysis confirms the presence of lanthanides in the precipitates and thus capture of the metal ions during the formation of the precipitates. Furthermore, the elemental analysis shows (see La/Lu ratio column) that some conditions, in particular the solids prepared in the presence of $CO_2$ and of aldehyde C, exhibit advantageous selectivity with respect to lutetium.

Reproducing the conditions of the final line of the table (C: 5: La/Lu in the presence of $CO_2$) in an isolated handling operation (that is to say, not in a library) made it possible to increase the La/Lu selectivity up to 2.52.

The procedure employed is as follows:

12.6 mg of C ($6\times10^{-5}$ mol) are placed in 3 ml of methanol and 12 µl of butylamine ($1.2\times10^{-4}$ mol) are added in order to dissolve the trisaldehyde. 17.43 mg of spermidine 5 ($1.2\times10^{-4}$ mol), 30.8 mg of Lu(CF$_3$CO$_2$)$_3$ ($3\times10^{-5}$ mol) and 28.7 mg of La(CF$_3$CO$_2$)$_3$ ($3\times10^{-5}$ mol) are added to the solution. $CO_2$ is bubbled into the solution until the appearance of the precipitate. The solid is centrifuged, washed three times with methanol and then dried under a stream of $CO_2$.

| Ln introduced | | Counteranion | Ln stochiometry | | ICP-MS measurement, % by weight | | % ratio of the weights involved[1] | | Ln1/Ln2 |
|---|---|---|---|---|---|---|---|---|---|
|  |  |  | La | Lu | La | Lu | La | Lu |  |
| La | Lu | CF$_3$CO$_2^-$ | 0.5 | 0.5 | 24.73 | 9.82 | 6.35 | 8.00 | 2.52 |

[1] Ratio of the weights involved = $w_M^0/(w_S^0 + w_B^0 + w_{NHBu}^0 + w_{CO2}^{max} + w_M^0)$ with $w_M^0$ the weight of metal introduced, $w_S^0$ the weight of the spermidine introduced, $w_C^0$ the weight of aldehyde introduced, $w_{NHBu}^0$ the weight of butylamine introduced and $w_{CO2}^{max}$ the maximum weight of $CO_2$ which can be captured.

The term ICP-MS denotes plasma torch mass spectrometry.

2) Analysis of the Influence of the Lanthanide Concentration on the Selectivity

Solids obtained in the presence of 1 and 0.5 equivalent of lanthanum and lutetium were analyzed by LC-MS. The libraries with 1 equivalent of La and Lu were prepared by mixing 1 ml of 60 mM aldehyde, 1 ml of 120 mM amine, 500 µl of 120 nM La(CF$_3$COO)$_3$ and 500 µl of 120 mM Lu(CF$_3$COO)$_3$. The libraries with 0.5 equivalent of La and Lu were prepared by mixing 1 ml of 60 mM aldehyde, 1 ml of 120 mM amine, 250 µl of 120 mM La(CF$_3$COO)$_3$, 250 µl of 120 mM Lu(CF$_3$COO)$_3$ and 500 µl of methanol. The assaying of the lanthanides carried out by LC-MS is presented in Table 2 below.

TABLE 2

Influence of the concentration of metal in the libraries on the selectivity
These results show in particular a good selectivity of the libraries prepared from aldehyde C. In addition, the decrease in the concentration of metal in the libraries results in an increase in the selectivity during the formation of the precipitates.

| Precipitate | Number of equivalents of metal | Amount (mg) | % by weight | | % of metal captured | | La/Lu ratio by weight |
|---|---|---|---|---|---|---|---|
|  |  |  | La | Lu | La | Lu |  |
| A:5:CO$_2$ | ½ | 30 | 4.99 | 7.44 | 35.9 | 42.5 | 0.67 |
| A:5:CO$_2$ | 1 | 4 | 4.39 | 9.16 | 2.1 | 3.5 | 0.48 |
| C:2:CO$_2$ | ½ | 7 | 0.14 | 3.29 | 0.2 | 4.4 | 0.04 |
| C:2:CO$_2$ | 1 | 13.1 | 2.45 | 8.90 | 3.8 | 11.11 | 0.27 |
| C:4:CO$_2$ | ½ | 4.7 | <threshold | 3.18 | / | 2.8 | / |
| C:4:CO$_2$ | 1 | 16.4 | 2.33 | 12.24 | 4.6 | 19.1 | 0.19 |
| C:5:CO$_2$ | ½ | 10 | 0.87 | 9.15 | 2.1 | 17.4 | 0.09 |
| C:5:CO$_2$ | 1 | 10.7 | 2.30 | 9.94 | 3.0 | 10.1 | 0.23 |
| C:6:CO$_2$ | 1 | 12.4 | 0.56 | 6.98 | 0.8 | 8.2 | 0.08 |

Example 4: Capturing Different Elements with Polyethylenimine

Procedures:

12 mg ($w_{In}^0$, $4\times10^{-5}$ mol) of $In(NO_3)_3$ are dissolved in 6 ml of absolute ethanol and 0.5 ml of 50% PEI (polyethylenimine, Mw=60,000 g/mol) in water ($w_{PEI}^0$=250 mg; $n_{PEI}^0$=4.1×10$^{-6}$ mol; 5.72×10$^{-3}$ mol of N; $n_{CO2}^{max}$=2.86× 10$^{-3}$; $n_{In}^{max}$=9.53×10$^{-4}$ mol) is added (clear solution). $CO_2$ is bubbled into the solution at atmospheric temperature and atmospheric pressure. The immediate formation of a precipitate is observed. The suspension is heated at 90° C. under $CO_2$ pressure until complete dissolution of the solid. The solution is then slowly brought back to ambient temperature. The solid is obtained by simple filtration, washing and drying under vacuum.

9.1 mg ($w_{Pr}^0$, 2.1×10$^{-5}$ mol) of $Pr(NO_3)_3$ and 10.3 mg ($w_{Lu}^0$, 2.8×10$^{-5}$ mol) of $Lu(NO_3)_3$ are dissolved in 6 ml of absolute ethanol and 0.5 ml of 50% PEI (polyethylenimine, Mw=60,000 g/mol) in water ($w_{PEI}^0$=250 mg, $n_{PEI}^0$=4.1× 10$^{-6}$ mol; 5.72×10$^{-3}$ mol of N; $n_{CO2}^{max}$=2.86×10$^{-3}$) is added (clear solution). $CO_2$ is bubbled into the solution at atmospheric temperature and atmospheric pressure. The immediate formation of a precipitate is observed. The suspension is heated at 90° C. under $CO_2$ pressure until complete dissolution of the solid. The solution is then slowly brought back to ambient temperature, which brings about the formation of a fresh solid. The solid is obtained by simple filtration, washing and drying under vacuum.

Results:

| T (° C.) | Element introduced | ICP-MS measurement, % by weight Ln1/Ln2 | Ratio of the weights involved[1] | | | Theoretical maximum % by weight[2] | | | % of metal captured |
|---|---|---|---|---|---|---|---|---|---|
| | | | In | Pr | Lu | In | Pr | Lu | In |
| 90 | In | | 1.02 | | | 1.18 | | | 22.54 | | | 100 |
| 25 | In | | 0.78 | | | 1.18 | | | 22.54 | | | 95 |
| 90 | Pr Lu | 0.75 | | 0.74 | 0.98 | | 0.73 | 0.91 | | 12.57 | 15.61 | |

[1]Ratio of the weights involved = $w_M^0/(w_{PEI}^0 + w_M^0 + w_{CO2}^{max})$ with $w_M^0$ the weight of metal introduced and $w_{PEI}^0$ the weight of PEI introduced.
[2]Theoretical maximum % by weight = $w_M^{max}/(w_{PEI}^0 + w_M^{max} + w_{CO2}^{max})$ with $w_M^{max}$ the maximum weight of metal which can be captured and $w_{CO2}^{max}$ the maximum weight of $CO_2$ which can be captured, for a weight of PEI equal to $w_{PEI}^0$.

The PEI made possible the capture of In, Pr and Lu. The contents of metals in the solids analyzed are low (less than 1%). However, they are of the same order of magnitude as the ratio by weight of PEI to weight of metal used for the capturing and are consistent with the increase in weight of the polymer by absorption of $CO_2$. In the case of indium, the solids obtained by slow precipitation (fall in temperature from 90° C.) have a higher content of metal than the solids obtained by capture at ambient temperature. The selectivity between Pr and Lu is in favor of Lu with a Pr/Lu ratio of 0.75.

Example 5: Capturing Different Elements with Amines of Low Molecular Weight

The following amines are used:
TETA: Triethylenetetramine:

DETA: Diethylenetriamine:

En: Ethylenediamine:

Tren: Tris(2-aminoethyl)amine:

Procedure:

An amount of metal of between 0.13 and 0.04 is added to a solution of amine ($n_A$=6×10$^{-4}$ mol) in 5 ml of absolute ethanol. $CO_2$ is bubbled into the solution at atmospheric temperature and atmospheric pressure. The suspension is heated at 90° C. under $CO_2$ pressure until a complete dissolution of the solid. The solution is then slowly brought back to ambient temperature (1 to 2° C./min) in order to bring about the precipitation. The solid is obtained by filtration, washing with absolute ethanol and drying under vacuum.

Results:

The reversibility of the solids was confirmed during the heating of the suspension at 90° C. The solids formed during the slow fall in temperature were analyzed by ICP-MS (see table below).

| T (° C.) | Amine used | Element introduced | Counterion | $n_A/n_M$ | ICP-MS measurement, % by weight | | Ratio of the weights involved[1] in % | | Theoretical maximum % by weight[2] | | % of metal captured |
|---|---|---|---|---|---|---|---|---|---|---|---|
| | | | | | In | Nd | In | Nd | In | Nd | In |
| 90 | TETA | In | $NO_3^-$ | 6 | 3.45 | | 7.55 | | 24.63 | | 53 |
| 90 | TETA | Nd | $NO_3^-$ | 24 | | 2.36 | | 3.30 | | 29.10 | |
| 90 | TETA | Nd | $^-OAc$ | 12 | | 6.10 | | 4.88 | | 29.10 | |
| 90 | TETA | Nd | $CF_3CO_2^-$ | 6 | | 14.25 | | 9.31 | | 29.10 | |
| 90 | Tren | In | $NO_3^-$ | 6 | 2.38 | | 8.27 | | 21.29 | | 20 |
| 90 | DETA | In | $NO_3^-$ | 6 | 6.55 | | 10.16 | | 25.34 | | 56 |
| 90 | En | In | $NO_3^-$ | 24 | 5.01 | | 4.39 | | 26.88 | | 58 |
| 25 | TETA | In | $NO_3^-$ | 6 | 1.52 | | 7.55 | | 24.63 | | 88 |
| 25 | TETA | Nd | $NO_3^-$ | 24 | | 2.02 | | 3.30 | | 29.10 | |
| 25 | TETA | Nd | $^-OAc$ | 12 | | 3.06 | | 4.88 | | 29.10 | |
| 25 | TETA | Nd | $CF_3CO_2^-$ | 6 | | 6.64 | | 9.31 | | 29.10 | |
| 25 | Tren | In | $NO_3^-$ | 6 | 12.35 | | 8.27 | | 21.29 | | 51 |
| 25 | DETA | In | $NO_3^-$ | 6 | 2.98 | | 10.16 | | 25.34 | | 71 |
| 25 | En | In | $NO_3^-$ | 24 | 3.49 | | 4.39 | | 26.88 | | 100 |

[1]Ratio of the weights involved = $w_M^0/(w_A^0 + w_{CO2}^{max} + w_M^0)$ with $w_M^0$ the weight of metal introduced, $w_A^0$ the weight of amine introduced and $w_{CO2}^{max}$ the maximum weight of $CO_2$ which can be captured with a weight $w_A^0$ of amine involved.
[2]Theoretical maximum % by weight = $w_M^{max}/(w_A^0 + w_M^{max} + w_{CO2}^{max})$ with $w_M^{max}$ the maximum weight of metal which can be captured and $w_{CO2}^{max}$ the maximum weight of $CO_2$ which can be captured with a weight $w_A^0$ of amine involved.

The carbamates of amines having from two to four nitrogen sites made it possible to capture In and Nd, the contents of metals varying between 2 and 15% according to the metal, the counterion and the amine used.

In the case of Nd, the content of metal increases when the metal to amine ratio initially introduced increases, which means that the stoichiometries used are subsaturating. The values of the contents are similar to the ratios of the weights involved; in some cases, they are even greater than these ratios. It can be deduced therefrom, in these cases, that there exists a phenomenon of displacement of equilibrium and that a portion of the amine has remained in solution in the free form. A role of the counterion of the metal on the reversibility of the capturing according to the state (kinetic/thermodynamic) is also observed.

In the case of In, capturing is more effective at 90° C. in the case of the linear amines (En, DETA, TETA) and is more effective at AT in the case of Tren.

Example 6: Study of the Capture of in by the $A_2CO_2$ System 206.1 mg of trisimine $A1_3$ ($6 \times 10^{-4}$ mol) were dissolved in 10 ml of methanol and 129.6 μl of DETA ($1.2 \times 10^{-3}$ mol) and 54.76 mg of $In(NO_3)_3$ ($1.8 \times 10^{-4}$ mol) were added to the solution. $CO_2$ was bubbled into the solution until the appearance of a precipitate. The suspension was heated at reflux under a $CO_2$ atmosphere until complete dissolution of the solid. The solution was slowly cooled to ambient temperature. The solid formed was filtered off, washed with methanol and dried under vacuum.

| T (° C.) | Ln | ICP-MS measurement, % by weight | Ratio of the weights involved | Theoretical maximum % by weight |
|---|---|---|---|---|
| 90 | In | 2.42% | 7.58% | 19.75% |

The ICP-MS measurement shows that this system makes possible the reversible capture of In from a solution in alcohol.

The invention claimed is:

1. A process for capturing and separating at least one chemical element selected from p-block metals, alkali metals, alkaline earth metals, actinide metals and rare earth metals in a sample, the method comprising:
   1) contacting the sample comprising said at least one chemical element with:
      $CO_2$ and at least one amine containing at least two amine groups, or
      an adduct forming by contacting $CO_2$ and at least one amine containing at least two amine groups,
      to form a molecular assembly,
      said contacting performed in a solvent selected from water and alcohol,
   2) allowing the formation of a precipitate comprising said molecular assembly and separating the precipitate, and
   3) dissociating the components of the molecular assembly by heating at a temperature less than or equal to 100° C. or by hydrolysis so as to release from the molecular assembly said at least one chemical element.

2. The process of claim 1, in which at least one of the chemical elements is (a) rare earth metal(s).

3. The process of claim 1, in which at least one of the chemical elements is (a) rare earth metal(s) selected from lanthanum and lutetium.

4. The process of claim 1, in which the amine is of general formula (IV): $R_2$—NH—$R_3$, in which:
   $R_2$ is selected from alkyl, alkenyl, alkynyl, cycloalkyl, cycloalkenyl, cycloalkynyl and aromatic groups, the hydrocarbon chain of which is optionally interrupted by at least one heteroatom selected from N, O and S and which is optionally substituted by at least one substituent, and
   $R_3$ is selected from a hydrogen atom, alkyl, alkenyl, alkynyl, cycloalkyl, cycloalkenyl, cycloalkynyl and aromatic groups, the hydrocarbon chain of which is optionally interrupted by at least one heteroatom selected from N, O and S and which is optionally substituted by at least one substituent, which substituent does not comprise an aldehyde CHO.

5. The process of claim 4, in which $R_2$ is a linear alkyl group, the hydrocarbon chain of which is optionally interrupted by at least one heteroatom selected from N, O and S and which is optionally substituted by at least one substituent, and $R_3$ is a hydrogen atom.

6. The process of claim 1, in which the amine is selected from the compounds ethylenediamine tris(2-aminoethyl)amine diethylenetetramine triethylenetetramine piperazine cis-1,4-cyclohexanediamine trans-1,4-cyclohexanediamine and phenylenediamine 7. The process of claim 1, said process comprising filtration and/or centrifugation to separate the precipitate from the reaction medium.

8. The process of claim 1, in which the separation makes it possible to liberate and/or reform at least one component selected from the amines and/or $CO_2$ forming the assembly, or one of their derivatives.

* * * * *